US006511510B1

(12) United States Patent
de Bruijn et al.

(10) Patent No.: US 6,511,510 B1
(45) Date of Patent: Jan. 28, 2003

(54) OSTEOINDUCTIVE CERAMIC MATERIALS (75) Inventors: Joost D. de Bruijn, Den Haag (NL); Klaas de Groot, Heemsdede (NL); Clemens A. van Blitterswijk, Hkendorp (NL); Yuan Huipin, Ziest (NL)

(73) Assignee: IsoTis N.V., Bilthoven (NL)

( * ) Notice: Subject to any disclaimer, the term of this patent is extended or adjusted under 35 U.S.C. 154(b) by 0 days.

(21) Appl. No.: 09/396,072

(22) Filed: Sep. 15, 1999

(30) Foreign Application Priority Data

Sep. 15, 1998 (EP) .............................. 98203084

(51) Int. Cl.$^7$ ................................. A61F 2/28
(52) U.S. Cl. ................. 623/23.56; 623/23.51; 623/23.61; 623/926
(58) Field of Search .............. 623/23.51, 23.56, 623/23.61, 908, 926; 523/116; 433/228.1

(56) References Cited

U.S. PATENT DOCUMENTS

| | | | |
|---|---|---|---|
| 4,195,366 A | 4/1980 | Jarcho et al. | |
| 4,629,464 A | 12/1986 | Takata et al. | 623/16 |
| 5,017,518 A | 5/1991 | Hirayama et al. | 501/1 |
| 5,096,814 A * | 3/1992 | Aivasidis et al. | 435/41 |
| 5,266,248 A * | 11/1993 | Ohtsuka et al. | 264/44 |
| 5,355,898 A | 10/1994 | Ripamonti | 128/898 |
| 5,531,794 A | 7/1996 | Takagi et al. | 623/16 |
| 5,549,123 A | 8/1996 | Okuyama et al. | 128/898 |
| 5,916,553 A * | 6/1999 | Schmidt | 424/85.1 |
| 6,149,688 A * | 11/2000 | Brosnahan et al. | 623/23.5 |

FOREIGN PATENT DOCUMENTS

| EP | 0 267 624 A2 | 5/1988 |
|---|---|---|
| EP | 0303262 A2 * | 2/1989 |
| EP | 1-93476 A * | 4/1989 |

OTHER PUBLICATIONS

Ata et al., "Magnetically Assisted Impaction Coating Process to Synthesize Engineered Particulates with Controlled Surface Characteristics," *Mat. Res. Soc. Symp. Proc.*, 501:333–338 (1996).

Chen et al., "The Histological Observation of the Early Osteogenesis Induced in Porous Calcium Phosphate Ceramics in Muscular Tissue of the Dogs," 115:233–236 (1996).

Hueghebaert et al., "Physiochemical characterization of deposits associated with HA ceramics implanted in nonosseous sites," *J. Biomed. Mater. Res.*, 22(A3):257–268 (1988).

Peelen et al., "Sintered hydroxylapatite as a bioceramic," *Philips tech. Rev.*, 37(9)/10:234–236 (1977).

Ripamonti, "The Induction of Bone in Osteogenic Composites of Bone Matrix and Porous Hydroxyapatite Replicas . . . ", *J. Oral Maxillofacial Surgery*, 49:817–830 (1991).

Ripamonti, "The Morphogenesis of Bone in Replicas of Porous Hydroxyapatite Obtained from Conversion of Calcium Carbonate Exoskeletons of Coral," *J. Bone and Joint Surgery*, 73–A(5):692–703 (1991).

Ripamonti and Reddi, "The Critical Role of Geometry of Porous Hydroxyapatite Delivery System in Induction of Bone by Osteogenin, a Bone Morphogenetic Protein," *Matrix*, 12:202–212 (1992).

(List continued on next page.)

*Primary Examiner*—Paul B. Prebilic
(74) *Attorney, Agent, or Firm*—Banner & Witcoff, Ltd.

(57) ABSTRACT

The invention relates to an osteoinductive biomaterial, which is based on a ceramic material and which has a total porosity of 20 to 90%, wherein macropores are present having a size ranging from 0.1 to 1.5 mm, and wherein micropores are present having a size ranging from 0.05 to 20 $\mu$m. The invention further relates to a process for preparing said osteoinductive biomaterial.

7 Claims, 6 Drawing Sheets

OTHER PUBLICATIONS

Ripamonti et al., "Expression of the Osteogenic Phenotype in Porous Hydroxyapatite Implanted Extraskeletally in Baboons," *Matrix*, 13:491–502 (1993).

Ripamonti et al., "Initiation of Heterotopic Osteogenesis in Primates after Chromatographic Adsorption of Osteogenin, a Bone Morphogenetic Protein, onto Porous Hydroxyapatite," *Biochem. and Biophys. Res. Comm.*, 193(2):509–517 (1993).

Ripamonti, "Osteoinduction in porous hydroxyapatite implanted in heterotopic sites of different animal models," *Biomaterials*, 17(1):31–35 (1996).

Yamasaki and Sakai, "Osteogenic response to porous hydroxyapatite ceramics under the skin of dogs," *Biomaterials*, 13(5):308–312 (1992).

Yang et al., "Osteogenesis in extraskeletally implanted porous calcium phosphate ceramics: variability among different kinds of animals," *Biomaterials*, 17(22):2131–2137 (1996).

Yokozeki et al., "Influence of surface microstructure on the reaction of the active ceramics in vivo," *E. Materials in Medicine*, 9:381–384 (1998).

Gaillard and van Blitterswijk, "Pre–operative addition of calcium ions or calcium phosphate crystals to PEO/PBT copolymers (Polyactive™) stimulates bone mineralization in vivo," *J. Mater. Sci.*, 5:695–701 (1994).

\* cited by examiner

OSTEOINDUCTIVE CERAMIC MATERIALS

The invention relates to an osteoinductive material and to a process for preparing said material.

Calcium phosphates such as hydroxyapatite are known to be osteoconductive, or bioactive. This means that they act as a template along which bone growth can occur. Further, bone formation can directly take place at the surface of the material, and a strong bond is obtained with bone tissue. Osteoinductivity, on the other hand, is regarded as a property of materials that induce the formation of bone tissue. In the past, this property has only been described in connection with materials that contain osteoinductive, proteinaceous factors such as bone morphogenetic proteins (BMP's).

Recently, however, several studies have been reported that indicate a possible osteoinductive capacity of calcium phosphates when implanted intramuscularly in dogs or baboons. Generally, it is assumed that the presence of a porous structure and a specific geometry of the implant plays a crucial role in the osteoinductive character of the implant.

Yamasaki et al., in Biomaterials 1992, vol. 13, no. 5, 308–312, have described to have found heterotopic bone formation around porous hydroxyapatite ceramic granules, but not around dense granules. The porous granules had a size between 200 and 600 $\mu$m, and a continuous and interconnected microporosity ranging in diameter from 2 to 10 $\mu$m.

The present invention aims to provide a material having an improved osteoinductivity. It is an object of the invention to provide a material that is suitable to be used as an implant in living organisms and to function as a (temporary) substitute for bone tissue. Thus, the material should be both biocompatible and biodegradable.

Surprisingly, it has been found that this object is achieved by the provision of a ceramic material having both macropores and micropores of specific sizes. Hence, the invention relates to an osteoinductive biomaterial, which is based on a ceramic material and which has a total porosity of 20 to 90%, wherein macropores are present having a size ranging from 0.1 to 1.5 mm, and wherein micropores are present having a size ranging from 0.05 to 20 $\mu$m.

The material of the invention shows excellent osteoinductive behaviour in living tissue. The formation of bone tissue at the surface of the material of the invention assists in a favourable acceptation of an implant made of said material. Moreover, the formation of the bone tissue accelerates the recovery of any damage in the bone structure, which forms the reason for applying the implant.

An osteoinductive biomaterial according to the invention is based on a ceramic material. The biomaterial may for instance be a medical implant formed of a ceramic material. It is also possible that the biomaterial is a medical implant of a different material, such as a metal or a polymeric material, on which the ceramic material is present in the form of a coating. Another possibility is described by M. L. Gaillard and C. A. van Blitterswijk in J. Mater. Sci., Materials in Medicine, 5:695–701 (1994). This possibility concerns a copolymer having hydrogel-like properties, which may be calcified in the presence of calcium and phosphate ions.

In principle, any ceramic material that is both sufficiently biocompatible and sufficiently biodegradable to be used as an implant in living tissue can be used. Preferably, the ceramic material is capable of providing a calcium phosphate surface, either in vitro or in vivo, which has the present specific surface structure. It is further preferred that the ceramic material is capable of adsorbing biologically active agents, such as growth factors (BMP's etc.), either in vitro or in vivo. Suitable examples of ceramic materials include calcium phosphates, glass ceramics and materials containing calcium phosphates and/or glass ceramics.

Preferably, the ceramic material is a calcium phosphate. Preferred calcium phosphates are octacalcium phosphate, apatites, such as hydroxyapatite and carbonate apatite, whitlockites, such as a-tricalcium phosphate and $\beta$-tricalcium phosphate, and combinations thereof.

An important aspect of the invention is the physical structure of the osteoinductive biomaterial. The material comprises both macropores and micropores. The total porosity ranges from 20 to 90%, preferably from 40 to 70%.

The macropores of the material have a size of from 0.1 to 1.5 mm. Preferably, the size of the macropores lies between 0.2 and 1 mm. It has been found that the indicated sizes of the macropores have a significant beneficial influence on the osteoinductive character of the material. Further preferred is that the macropores are interconnected.

The micropores of the material have a size of from 0.05 to 20 $\mu$m. Preferably, the micropores are at least located in the macropores. In accordance with this embodiment, the formation of bone tissue is highly promoted. A preferred range for the size of the micropores is from 0.5 and 10 $\mu$m. In a preferred embodiment, the micropores are at least present in the surface of the macropores. The microporosity of the material's surface preferably lies between 40 and 60%.

In accordance with the invention, the biomaterial preferably consists of crystals. Preferably, the size of the crystals is similar to the size of the micropores. When this is the case, the biomaterial has a preferable microrugosity. Thus, the size of the crystals lies preferably between 0.05 and 20 $\mu$m, more preferably between 0.5 and 10 $\mu$m.

The osteoinductive biomaterial according to the invention may advantageously be used in applications where bone formation is desired. Thus, the material may be used for the manufacture of medical implants, particular implants for bone substitution. The material may further be used for the manufacture of a scaffold for tissue engineering a bone equivalent.

The invention further relates to processes for preparing an osteoinductive biomaterial as described above.

In a first embodiment, the osteoinductive biomaterial may be prepared by sintering a ceramic material under such conditions, that an osteoinductive biomatieral as described above is obtained. The ceramic material is, before the sintering, in a calcined state. The sintering is preferably performed at a temperature between 1000 and 1275° C., treated with an aqueous solution of an organic acid and washed to remove the acid.

Preferably, the sintering is carried out at a temperature between 1150 and 1250° C. The duration of the sintering step may suitably be chosen between 6 and 10 hours, preferably between 7 and 9 hours. It has further been found advantageous to perform the sintering while the ceramic material is submersed in a powder of the ceramic material. This beneficially affects the reactivity of the surface of the material, and consequently also the bioactivity (dissolution, re-precipitation).

After the sintering, the material is preferably ground with sandpaper, such as Si—C sandpaper, to remove chemical surface impurities.

Subsequently, the material is treated with an aqueous solution of an acid. Suitable acids in this regard are any etching acids, i.e. any acids which lead to a slight dissolution of the calcium phosphate based material. The use of the following acids has been found to lead to extremely favourable results: maleic acid, hydrochloric acid, phosphoric acid, and combinations thereof. The concentration of the acid in the solution is preferably chosen such that the pH of the solution lies between 0 and 4, more preferably between 1 and 3.

After the acid treatment, which preferably lasts between 3 and 15 minutes, the ceramic material is washed to remove the acid. The washing may suitably be performed using ethanol, water or a combination thereof.

Finally, it is preferred to subject the obtained osteoinductive biomaterial to a sterilisation treatment, such as a steam sterilisation.

In a second embodiment, a slurry of a powder of the ceramic material in an aqueous solution of a negative replica forming agent, which during sintering burns or evaporates, is sintered under such conditions that an osteoinductive biomaterial as described above is obtained. Suitable negative replica forming agents include hydrogen peroxide, baking powder or bicarbonate. Preferably, hydrogen peroxide is used.

Thus, first, the powder is added to an aqueous solution of the negative replica forming agent to form a slurry. The concentration of the negative replica forming agent in the slurry preferably lies between 0.5 and 15 wt. %, more preferably between 1 and 5 wt. %, based on the weight of the solution. The powder is added in a ratio of between 0.5 to 5, preferably 1 to 3 grams per 1 milliliter of the solution. The slurry may then be cast in a mould having a desired shape and size and sintered. The sintering is preferably carried out at a temperature between 800 and 1300° C., more preferably between 1000 and 1200° C. for a period of up to 12 hours. Care should be taken that the sintering period is not so long that a dense material is obtained.

The invention will now be elucidated by the following, non-restrictive examples.

EXAMPLE 1

Preparation of Materials

Figure 1:
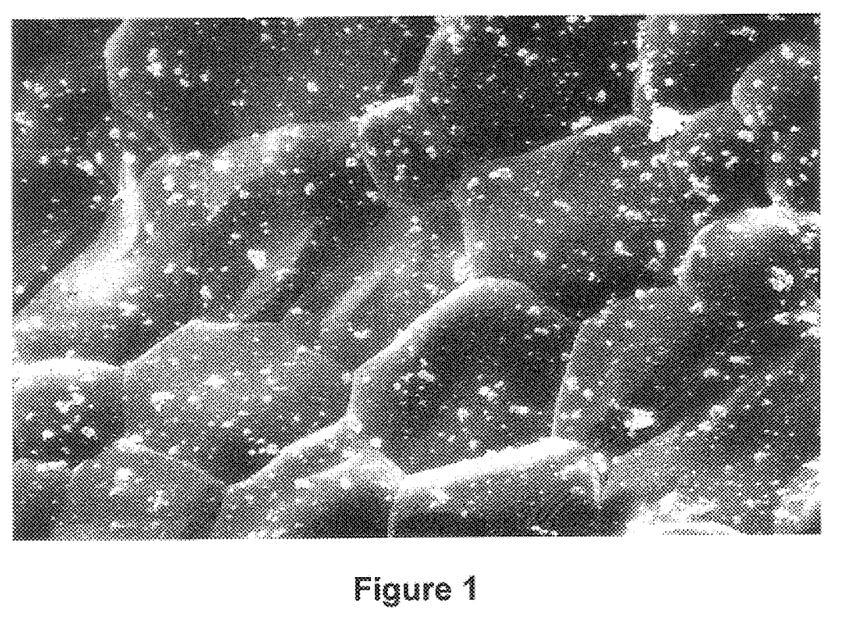
FIG. 1 is HA sintered at 1,300° C. and magnified 2,500 times.
Figure 2:
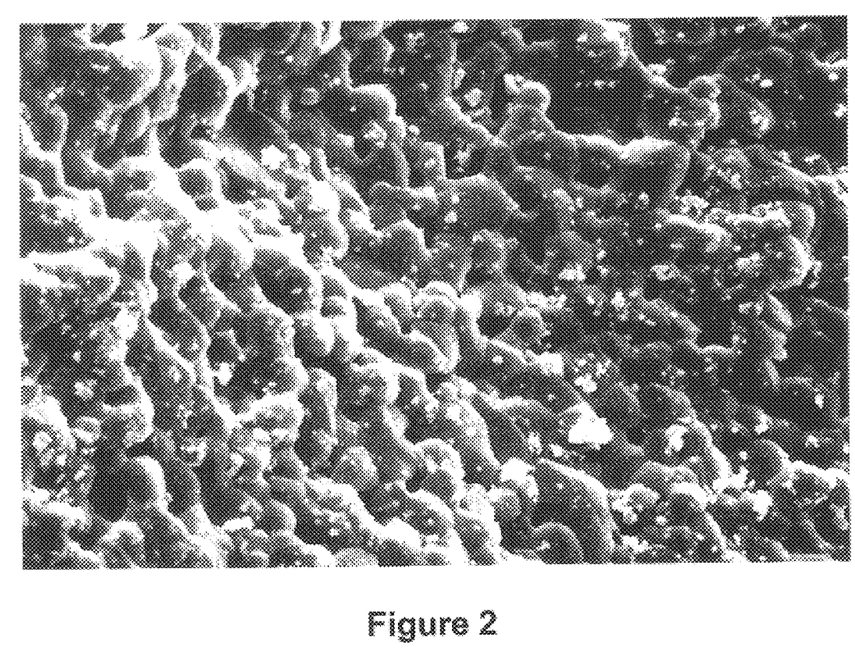
FIG. 2 is HA sintered at 1,250° C. and magnified 2,500 times.
Figure 3:
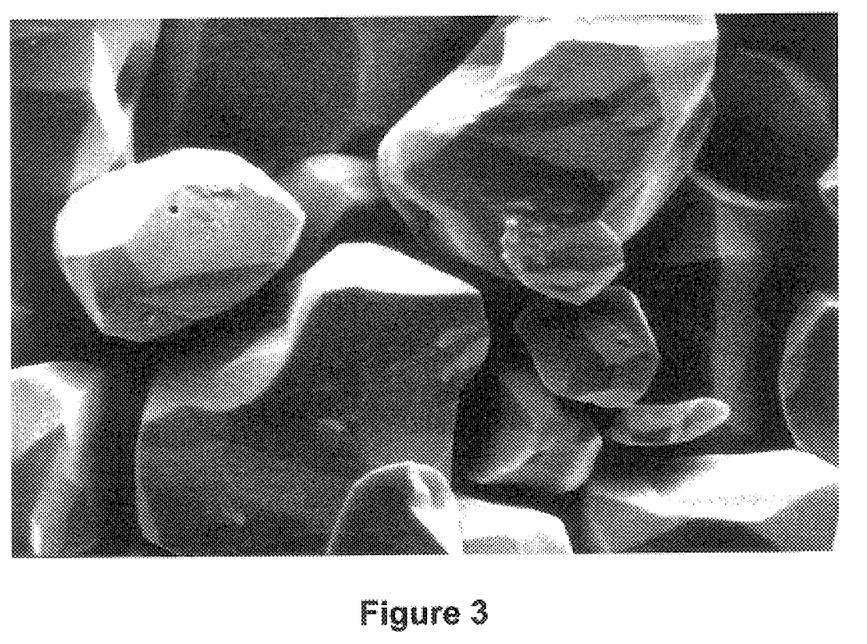
FIG. 3 is HA sintered at 1,300° C., treated with acid, and magnified 2,500 times.
Figure 4:
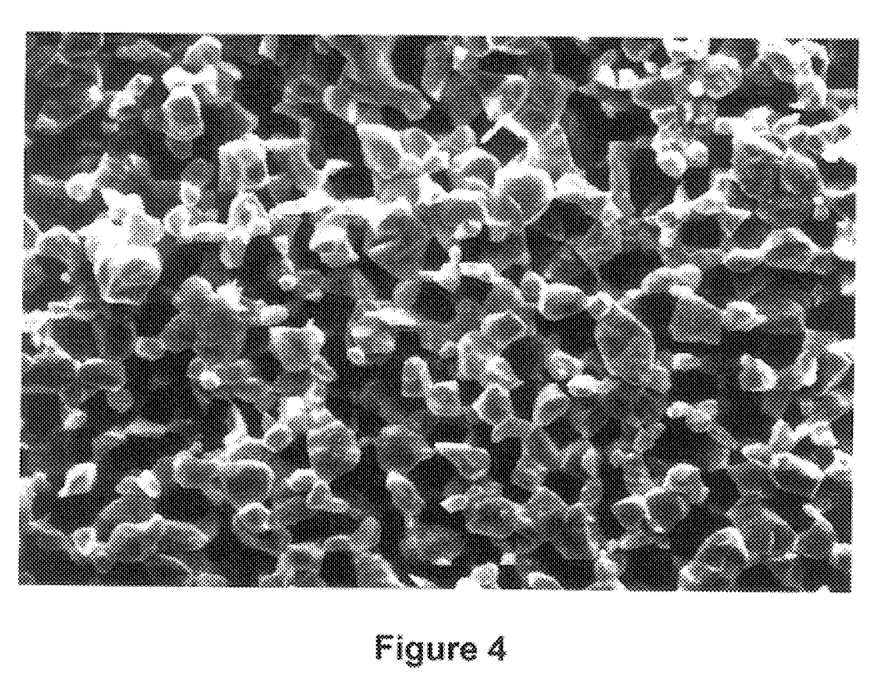
FIG. 4 is HA sintered at 1,250° C., treated with acid, and magnified 2,500 times.
Figure 5:
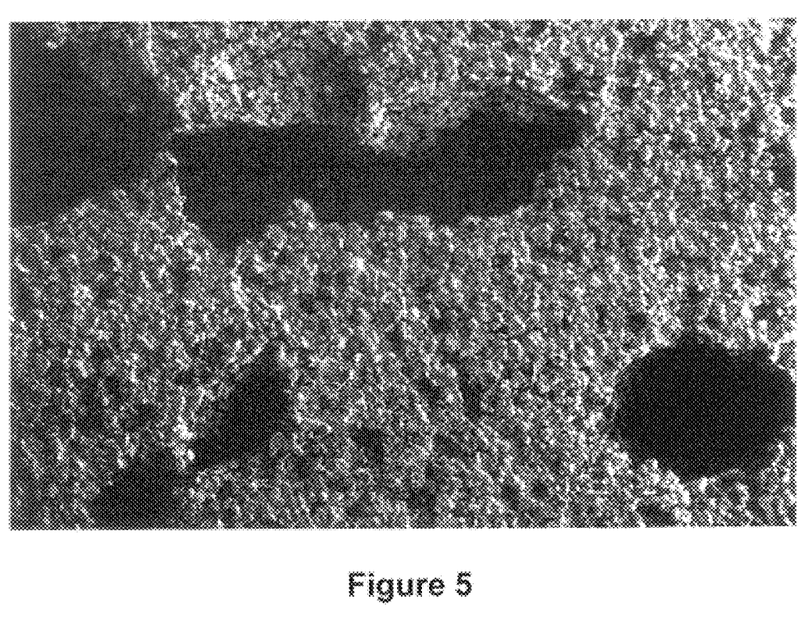
FIG. 5 is HA sintered at 1,300° C., treated with acid, and magnified 81.5 times.
Figure 6:
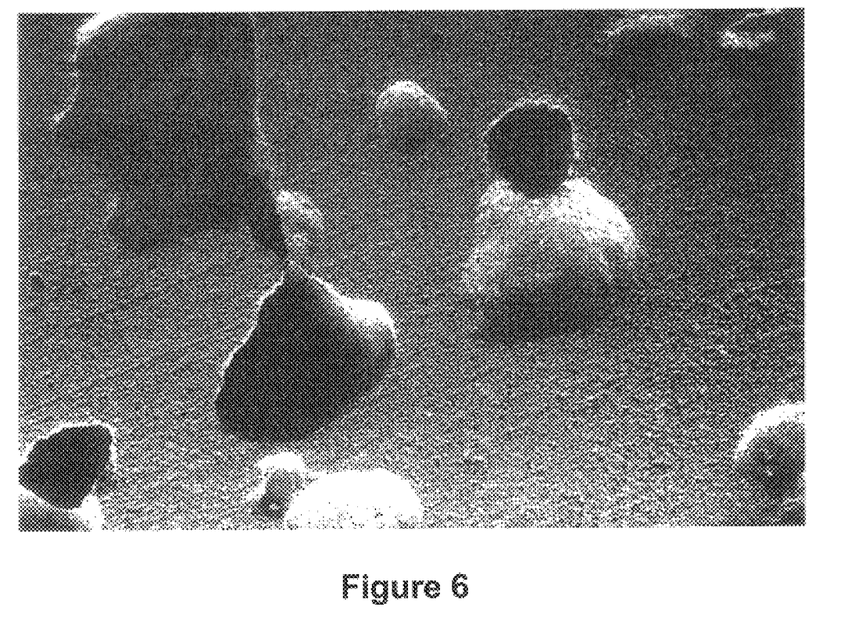
FIG. 6 is HA sintered at 1,250° C., treated with acid, and magnified 81.5 times.

Four different types of porous hydroxyapatite (HA) discs (approximately 6×6×2 mm in size) were prepared:
A: HA sintered at 1300° C. (FIG. 1)
B: HA sintered at 1250° C. (FIG. 2)
C: HA sintered at 1300° C., and treated with acid (FIGS. 3 and 5)
D: HA sintered at 1250° C., and treated with acid (FIGS. 4 and 6).
FIGS. 1–4 are 2500× enlarged; FIGS. 5 and 6 are 81.5× enlarged.

Two types of porous calcium phosphate blocks (18×18×25 mm) were prepared by sintering hydroxyapatite at either 1250° C. (HA1250; white colour) or 1300° C. (HA1300; blue colour). The HA1300 was prepared by a subsequent sintering of HA1250 blocks, for 8 hours at 1300° C. (the temperature was raised from room temperature by 100° C. per hour, kept constant for 8 hours, and lowered by 100° C. per hour to room temperature), while submersed in HA powder to obtain a surface reactive layer. HA1300 contained approximately 10–12% by weight of β-tricalcium phosphate. The sides of all blocks were ground with #220 Si—C sandpaper to remove chemical surface impurities, and the blocks were cut in 4 parts of approximately 8×8×25 mm. A total of twenty, 2 mm thick sections were prepared from each material type. The corners of each material (HA1250 and HA1300) were placed in 2.5% maleic acid for 10 minutes. Subsequently, all sections (40 in total) were ultrasonically cleaned/washed for 5 minutes in alcohol (70%) and distilled water respectively, individually packaged and sterilised by steam sterilisation.

Experimental Design and Surgical Procedure

Four pockets were created in the paravertrebal muscle in the back of 7 goats (2 pockets left and 2 pockets right from the spinal cord) for each of the four implants. the implants were inserted in a randomised manner in each pocket, ensuring that each implant type is only present once in each goat. Each material type was evaluated in sevenfold for statistical analysis, which necessitates the use of 7 goats.

Seven adult Dutch milk goats (approximately 40–60 kg; CAE/CL arthritis free and examined by a veterinary surgeon) were obtained from a professional stock breeder, and kept in quarantine for 4 weeks prior to the experiment. Prior to surgery, the goats were weighed and amphicilin 20% (2 ml/50 kg body weight) was administered by intramuscular injection. The surgical procedure was performed under general inhalation anaesthesia. After an intravenous injection of Thiopental, a mixture of nitrous oxide, oxygen and fluothane maintained anaesthesia. Left and right, 10 cm from the spinal cord, the back of each goat was shaved at two places, respectively. For each of the four intramuscular implantation sites (in each goat), an incision of approximately 3 cm was made, followed by blunt dissection until the muscle fascia of the paravertrebal muscle was reached. using a Mayo scissors, an incision of 15 mm was made in the muscle fascia and an intramuscular pocket was subsequently prepared by blunt dissection followed by implant insertion. The muscle fascia and skin were closed in separate layers using vicryl 3-0 sutures. Six months post-operatively, the animals were sacrificed using an intravenously administered overdose of thiopental and potassium chloride.

Implant Processing and Histology

After sacrificing the animals, the implants were excises. Six implants of each material type were placed in Karnovsky's fixative for at least one week (4° C.), while the seventh implant was stored at −70° C. for biochemical analysis. The fixed implants were subsequently dehydrated through a series of ethanol and embedded in Methyl Methacrylate. Semi-thin sections were cut on a modified innerlock diamond saw, perpendicular to the longitudinal plane of the implants, and examined by light microscopy for de novo bone formation.

Results

After the six months implantation time, histology revealed that a thin fibrous tissue capsule surrounded the HA samples. The adjoining muscle tissue had a normal appearance. None of the HA1250 and HA1300 sample revealed signs of degradation. With the acid treated HA1250 samples, some loosened HA particles could be observed at the periphery of the implant, while abundant surface degradation was observed with the acid treated HA1300. Especially at the outer surface of these implants, many loosened HA particles were present in the surrounding tissues. Noteworthy is the finding that particularly at both the outer surface and the pore surfaces of acid treated HA1250 implants, numerous individual mononucleated and multinucleated giant cells were present that were more or less cubicoidal in morphology. Furthermore, in the acid treated HA1250 samples, de novo bone formation was apparent. This bone tissue was normal in appearance and contained osteoblasts and osteocytes. None of the other materials revealed any bone formation.

EXAMPLE 2

Preparation of Material

A 2.0 M solution (A) of calcium nitrate tetra-hydrate (AR) in distilled water (AD) was prepared. A 2.0 M second solution (B) was prepared of diammonium hydrogen phosphate (AR) was prepared in distilled water (AD). Under stirring and adjusting the pH just over 8.0 using ammonia (AR), the second solution (B) was slowly added to the first solution (A) in a ratio of 1.63:1 (vol/vol).

The obtained mixed solution was kept overnight in a cupboard at ambient temperature. The next day, the pH of the solution was adjusted to over 10.00 using ammonia. The solution was left to age at ambient temperature.

After 30 days, the clear solution was tipped to leave a slurry which was washed five times. with distilled water (AD). Next, the slurry was filtered over 3 filter papers (2* #3 and 1* #1) under negative pressure. The cake in the filter was washed three times with distilled water (AD) while taken care that in between each washing cycle the filter cake was dry but not broken. The cake was then dried in an oven at 50° C. and ground to a powder. The resulting powder was sieved over a 140 mesh sifter to obtain a biphasic calcium phosphate (BCP) powder.

The BCP powder was mixed with a 3.0% aqueous hydrogen peroxide solution at a ratio of 1 gram powder in 1 ml solution. The resulting slurry was poured into a mould consisting of a plastic container (diameter 38 mm, height 60 mm). The mould was placed in an oven at 60° C. for foaming and drying. Next, the dry porous blocks were carefully removed from the container and sintered at 1100° C. for 10 hours (the temperature was raised from room temperature to 1100° C. in 10 hours, and after sintering, the temperature was decreased to room temperature in the same time frame.)

Animal Experiments

To test the osteoinductivity of the above prepared biphasic calcium phosphate (BCP), BCP cylinders were implanted in the thigh muscles of dogs for 90 days. Bone formation induced by BCP was analysed with histology, back scattered electron microscopy (BSE) and energy disperse X-ray (EDX) microanalysis.

1. Preparation of the Implants BCP blocks machined from BCP ceramic body as obtained above were polished into cylinders (5 mm diameter, 6 mm length). The implants were ultrasonically washed with 70% ethanol for 15 minutes, with demineralised water twice (15 minutes each), dried at 50° C., and then steam sterilised (121° C.) for 30 minutes before implantation.

2. Animal Preparation Eight healthy dogs (male and female, 2–6 years old, 10–15 kg) were selected and used to test the osteoinductivity of BCP.

3. Surgical Procedure

The surgical procedure was performed under general anaesthesia (30 mg pentobarbital sodium/kg body weight) and under sterile conditions. After shaving, the skin was sterilised with iodine and 70% ethanol. With a scalpel, a longitudinal incision was made in the skin. By a blunt separation, the thigh muscle was disposed. Again, with a scalpel, a small longitudinal incision was made in the thigh muscle and a muscle pouch was obtained by blunt separation. One BCP cylinder was inserted into the muscle pouch (one BCP implant was implanted in each dog). The surgical procedure was finished by suturing the muscle pouch and skin in layers with silk thread. The animals were intramuscularly injected with 1.6 million units penicillin 3 times in 3 days.

4. Sample Harvest

Ninety days after surgery, the dogs were sacrificed by an overdose of pentobarbital sodium, and the implanted samples with surrounding tissues were harvested and immediately fixed in 4% buffered (pH=7.4) formaldehyde. A total of 8 samples were collected from 8 dogs.

5. Histological Preparation

The fixed samples were washed with PBS (3 changes of PBS, 2 days each), then dehydrated with series ethanol solution (70%, 80%, 90%, 96% and 100%×2) and embedded in MMA. Thin undecalcified sections (10–20 micrometer) were made and stained with Methylene Blue and Basic Fuchsin for histological observation. Some sections were coated with carbon and observed with BSE and EDX.

6. Results

Incidence of Bone Formation

Bone formation was found in all samples (8 in 8) Identification of induced bone

Histologically, bone was found in the pores inside the implants. Mineralised bone matrix, osteoblast seams and osteocytes were obvious. BSE observation showed that the bone tissue was mineralised and contained osteocyte lacunas, EDX analysis showed that the mineralised tissues were composed of Ca and P.

7. Conclusion

Soft tissue implantation (both intramuscularly and subcutaneously) is the study model of osteoinduction. The bone formation in BCP ceramic followed intramuscular implantation showed that the tested BCP is osteoinductive.

EXAMPLE 3

Preparation of Material

A mixture was prepared of $SiO_2$ (relative amount 29.4% in weight, AR, particle size 0.5–10 microns), $NaHCO_3$ (relative amount 34.1% in weight, AR), $CaCO_3$ (relative amount 28.6% in weight, AR) and $Na_2HPO_4$ (relative amount 7.9% in weight, AR). This mixture was sintered for 10 hours at 1000° C. and for 2 hours at 1300° C. After cooling, a glass ceramic material was obtained.

The glass ceramic was broken mechanically into small particles, which were subsequently ball-milled to a fine powder. The powder was sieved through a 200 mesh filter. The glass ceramic powder was mixed with a 3.0% aqueous hydrogen peroxide solution at a ratio of 2.4 gram powder in 1 ml solution. The resulting slurry was poured into a plastic container (diameter 38 mm, height 60 mm). The mould was placed in an oven at 50° C. for foaming and drying. Next, the dry porous blocks were sintered at 800–1000° C. for 2 hours (the increase in temperature was 5° C./min.). Eventually, the blocks were allowed to cool naturally in the oven.

Animal Experiments

To test the osteoinductivity of the above prepared glass ceramics, glass ceramic cylinders were implanted in the thigh muscles of dogs for 90 days. Bone formation induced by glass ceramics was analysed with histology, back scattered electron microscopy (BSE) and energy disperse X-ray (EDX) microanalysis.

1. Preparation of the Implants

Glass ceramic blocks machined from glass ceramic body as prepared above were polished into cylinders (5 mm diameter, 6 mm length). The implants were ultrasonically washed with 70% ethanol for 15 minutes, with demineralised water twice (15 minutes each), dried at 50° C., and then steam sterilised (121° C.) for 30 minutes before implantation.

2. Animal Preparation

Eight health dogs (male and female, 2–6 years old, 10–15 kg) were selected and used to test the osteoinductivity of glass ceramic.

3. Surgical Procedure

Surgery was performed under general anaesthesia (30 mg pentobarbital sodium/kg body weight) and under sterile conditions. After shaving, the skin was sterilised with iodine ethanol and 70% ethanol. With a scalpel, a longitudinal incision was made in the skin. By a blunt separation, the thigh muscle was disposed. Again, with a scalpel, a small longitudinal incision was made in the thigh muscle, a muscle pouch was obtained by blunt separation. One glass ceramic cylinder was inserted into the muscle pouch (one implant was implanted in each dog). The surgical procedure was finished by suturing the muscle pouch and skin with silk thread in layers. The animals were intramuscularly injected with 1.6 million units penicillin for 3 days.

4. Sample Harvest

Ninety days after surgery, the dogs were sacrificed by a pentobarbital sodium overdose, and the implanted samples were harvested with surrounding tissues and immediately fixed in 4% buffered (pH=7.4) formaldehyde. A total of 8 samples were collected from 8 dogs.

5. Histological Preparation

The fixed samples were washed with PBS (3 changes of PBS, 2 days each), then dehydrated with series ethanol solution (70%, 80%, 90%, 96% and 100%×2) and embedded in MMA. Thin undecalified sections (10–20 micrometer) was made and stained with Methylene Blue and Basic Fuchsin for histological observation. Some sections were coated with carbon and observed with PSE and EDX.

6. Results

Incidence of bone formation

Bone formation was found in 6 samples of 8 Identification of induced bone

Histologically, bone was found in the pores inside the implants. Mineralised bone matrix, osteoblast seam and osteocytes were obvious. BSE observation showed that the bone tissues were mineralised with osteocyte lacunas, EDX analysis showed that the mineralised tissues were composed of Ca and P.

7. Conclusion

Soft tissue implantation (both intramuscularly and subcutaneously) is the study model of osteoinduction. The bone formation in glass ceramic followed intramuscular implantation showed that the tested glass ceramic is osteoinductive.

What is claimed is:

1. A method of inducing bone formation in a mammal comprising implanting an osteoinductive biomaterial into a mammal in a manner to induce bone formation on the osteoinductive biomaterial, wherein the osteoinductive biomaterial comprises a ceramic material having a total porosity of between 20% to 90% and a microporosity of the material's surface of between 40% to 60%, and comprises crystals having a crystal size of between 0.05 $\mu$m to 20 $\mu$m, and wherein the ceramic material comprises macropores having a size ranging from 0.1 mm to 1.5 mm, and micropores in the surface of the macropores, wherein the micropores have a size ranging from 0.05 $\mu$m to 20 $\mu$m.

2. The method of claim 1, wherein the macropores range in size from between 0.2 mm to 1.0 mm.

3. The method of claim 1, wherein the micropores range in size from between 0.5 $\mu$m to 10 $\mu$m.

4. The method of claim 1, wherein the total porosity is between 40% to 70%.

5. The method of claim 1, wherein the crystal size is between 0.5 $\mu$m to 10 $\mu$m.

6. The method of claim 1, wherein the ceramic material comprises calcium phosphate or glass ceramic.

7. The method of claim 1, wherein the ceramic material is one or more calcium phosphates selected from the group consisting of octacalcium phosphate, apatites, hydroxyapatite, carbonate apatite, whitlockites, $\beta$-tricalcium phosphate and $\alpha$-tricalcium phosphate.

* * * * *